under 35 U.S.C. 154(b) by 1188 days.

(12) United States Patent
Farrow et al.

(10) Patent No.: US 8,252,067 B2
(45) Date of Patent: Aug. 28, 2012

(54) QUICK-RELEASE COMPUTER ACCESS COVER

(75) Inventors: Timothy S. Farrow, Cary, NC (US); William F. Martin-Otto, Apex, NC (US)

(73) Assignee: Lenovo (Singapore) Pte. Ltd., Singapore (SG)

(*) Notice: Subject to any disclaimer, the term of this patent is extended or adjusted under 35 U.S.C. 154(b) by 1188 days.

(21) Appl. No.: 12/057,957

(22) Filed: Mar. 28, 2008

(65) Prior Publication Data

US 2009/0249495 A1    Oct. 1, 2009

(51) Int. Cl.
*G06F 21/02*    (2006.01)
(52) U.S. Cl. ............... 726/35; 713/194; 49/45; 49/57; 70/42; 70/79; 70/158
(58) Field of Classification Search ............ 726/25, 726/35; 713/194; 361/679.01, 679.02; 49/45, 49/57; 70/42, 79, 158
See application file for complete search history.

(56) References Cited

U.S. PATENT DOCUMENTS

| | | | | |
|---|---|---|---|---|
| 6,015,195 | A * | 1/2000 | Anderson et al. | 312/223.2 |
| 7,471,508 | B2 * | 12/2008 | Martin-Otto | 361/679.55 |
| 7,894,186 | B2 * | 2/2011 | Farrow et al. | 361/679.57 |

* cited by examiner

*Primary Examiner* — Eleni Shiferaw
*Assistant Examiner* — Paul Callahan
(74) *Attorney, Agent, or Firm* — Ference & Associates LLC

(57) ABSTRACT

A latch and latch handle recessed into the computer cover is provided, with the latch handle preferably presently a cam surface internally that interacts with a compatible cam surface associated with a lock bar. Preferably, a key lock is functionally integrated with the latch in such a way that when the key lock is unlocked the latch handle and latch are free to displace and to then urge the retention bar to disengage detents or hooks from slots or receptacles, by way of releasing the cover from a chassis or body of the desktop or workstation. Accordingly, in essentially one efficient movement via engaging the latch handle, a user will be able to quickly remove the cover.

20 Claims, 12 Drawing Sheets

QUICK-RELEASE COMPUTER ACCESS COVER

FIELD OF THE INVENTION

The present invention relates generally to locking and covering arrangements for computer desktops and workstations and the like.

BACKGROUND OF THE INVENTION

Computer workstations and desktops often contain highly sensitive components and data that often need to be kept secure from unauthorized personnel or users. Thus, the workstations and desktops often include access covers with locking mechanisms to inhibit or prevent unauthorized access.

In many conventional arrangements, a padlock or laptop-type lock (often known as a "Kensington lock") is used without the benefit of an added secondary or "backup" lock. However, even in those cases where a secondary or backup lock is included a rather cumbersome arrangement may be afforded. For instance a padlock provision may be afforded to the access cover while a key lock is also provided in the cover. The key lock is helpful because the padlock arrangement does not readily prevent a user from opening the cover sufficiently to still gain access to the computer components inside the cover. However, this dual arrangement can often be inconvenient to manage, and leaves tremendous room for improvement.

Other problems have long been noted with desktop or workstation access covers, in that the removal of a cover is normally accomplished solely through cumbersome and awkward physical movements and manipulations. Another compelling need has thus been recognized in connection with being able to remove a cover more quickly and efficiently, with minimized physical manipulation on the part of the user.

SUMMARY OF THE INVENTION

In accordance with at least one presently preferred embodiment of the present invention, there is broadly contemplated herein the provision of a latch and latch handle recessed into the computer cover, with the latch handle preferably presently a cam surface internally that interacts with a compatible cam surface associated with a lock bar. Preferably, a key lock is functionally integrated with the latch in such a way that when the key lock is unlocked the latch handle and latch are free to displace and to then urge the retention bar to disengage detents or hooks from slots or receptacles, by way of releasing the cover from a chassis or body of the desktop or workstation. Accordingly, in essentially one efficient movement via engaging the latch handle, a user will be able to quickly remove the cover.

In summary, one aspect of the invention provides an apparatus comprising: a main memory; a system processor; a chassis; a cover which is displaceable with respect to said chassis; said chassis and cover combining to substantially encase said main memory and system processor; a decoupling arrangement which selectively decouples said cover with respect to said chassis; a latch mechanism mounted at said cover; said latch mechanism comprising a latch which is displaceable with respect to said cover; said latch and said decoupling arrangement being operatively connected such that: in a first position of said latch, said decoupling arrangement couples said cover to said chassis; and in a second position of said latch, said decoupling arrangement decouples said cover from said chassis; said latch mechanism further comprising a locking arrangement which selectively locks and unlocks said latch, wherein: in a first configuration of said locking arrangement, said latch is not free to displace from said first position to said second position; and in a second configuration of said locking arrangement, said latch is free to displace from said first position to said second position.

Furthermore, an additional aspect of the invention provides a method of removing a computer cover, said method comprising: providing a chassis; providing a cover which is displaceable with respect to the chassis; providing a decoupling arrangement which selectively decouples the cover with respect to the chassis; providing a latch displaceably mounted with respect to the cover; operatively connecting the latch and the decoupling arrangement such that: in a first position of the latch, the decoupling arrangement couples the cover to the chassis; and in a second position of the latch, the decoupling arrangement decouples the cover from the chassis; coupling the cover with respect to the chassis; locking the latch into the first position; unlocking the latch to permit the latch to displace from the first position to the second position; and thereafter displacing the latch from the first position to the second position to thereby cause the decoupling arrangement to decouple the cover with respect to the chassis.

For a better understanding of the present invention, together with other and further features and advantages thereof, reference is made to the following description, taken in conjunction with the accompanying drawings, and the scope of the invention will be pointed out in the appended claims.

DETAILED DESCRIPTION OF THE PREFERRED EMBODIMENTS

For a better understanding of the present invention, together with other and further features and advantages thereof, reference is made to the following description, taken in conjunction with the accompanying drawings, and the scope of the invention will be pointed out in the appended claims.

Figure 1:
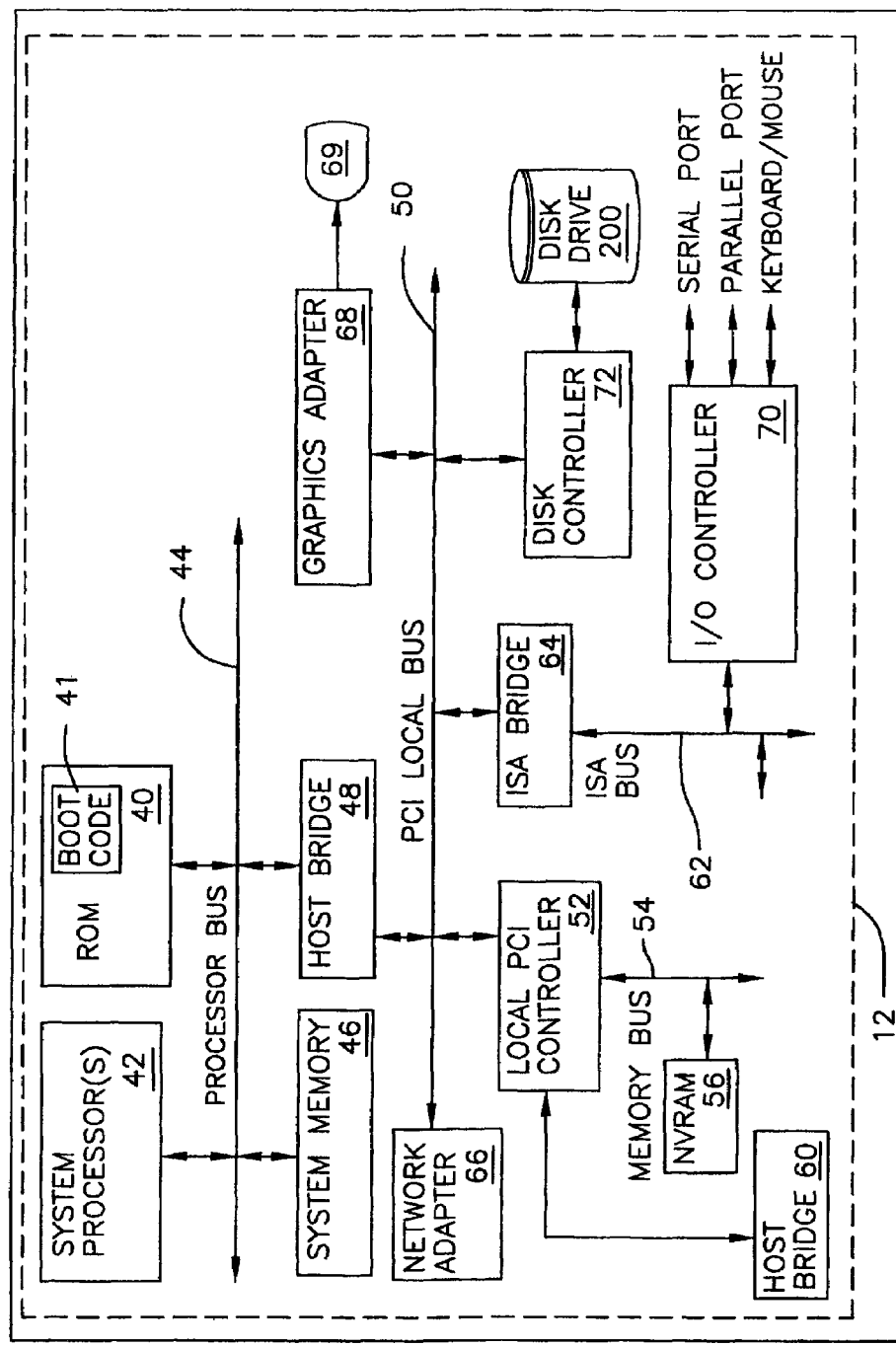
FIG. 1 schematically illustrates a computer system.

It will be readily understood that the components of the present invention, as generally described and illustrated in the Figures herein, may be arranged and designed in a wide variety of different configurations. Thus, the following more detailed description of the embodiments of the apparatus, system, and method of the present invention, as represented in FIGS. 1 through #, is not intended to limit the scope of the invention, as claimed, but is merely representative of selected embodiments of the invention.

Reference throughout this specification to "one embodiment" or "an embodiment" (or the like) means that a particular feature, structure, or characteristic described in connection with the embodiment is included in at least one embodiment of the present invention. Thus, appearances of the phrases "in one embodiment" or "in an embodiment" in various places throughout this specification are not necessarily all referring to the same embodiment.

Furthermore, the described features, structures, or characteristics may be combined in any suitable manner in one or more embodiments. In the following description, numerous specific details are provided, such as examples of different manners of locking and unlocking a computer cover, and of detaching a computer cover from a body or chassis to remove the cover. One skilled in the relevant art will recognize, however, that the invention can be practiced without one or more of the specific details, or with other methods, components, materials, etc. In other instances, well-known structures, materials, or operations are not shown or described in detail to avoid obscuring aspects of the invention.

The illustrated embodiments of the invention will be best understood by reference to the drawings, wherein like parts are designated by like numerals or other labels throughout. The following description is intended only by way of example, and simply illustrates certain selected embodiments of devices, systems, and processes that are consistent with the invention as claimed herein.

Referring now to FIG. 1, there is depicted a block diagram of an illustrative embodiment of a computer system 12. The illustrative embodiment depicted in FIG. 1 may be a notebook computer system, such as one of the ThinkPad® series of personal computers sold by Lenovo (US) Inc. of Morrisville, N.C., however, as will become apparent from the following description, the present invention is applicable to any data processing system, including a desktop or workstation computer. Notebook computers may alternatively be referred to as "notebooks", "laptops", "laptop computers" or "mobile computers" herein, and these terms should be understood as being essentially interchangeable with one another.

As shown in FIG. 1, computer system 12 includes at least one system processor 42, which is coupled to a Read-Only Memory (ROM) 40 and a system memory 46 by a processor bus 44. System processor 42, which may comprise one of the AMD™ line of processors produced by AMD Corporation or a processor produced by Intel Corporation, is a general-purpose processor that executes boot code 41 stored within ROM 40 at power-on and thereafter processes data under the control of operating system and application software stored in system memory 46. System processor 42 is coupled via processor bus 44 and host bridge 48 to Peripheral Component Interconnect (PCI) local bus 50.

PCI local bus 50 supports the attachment of a number of devices, including adapters and bridges. Among these devices is network adapter 66, which interfaces computer system 12 to a LAN, and graphics adapter 68, which interfaces computer system 12 to display 69. Communication on PCI local bus 50 is governed by local PCI controller 52, which is in turn coupled to non-volatile random access memory (NVRAM) 56 via memory bus 54. Local PCI controller 52 can be coupled to additional buses and devices via a second host bridge 60.

Computer system 12 further includes Industry Standard Architecture (ISA) bus 62, which is coupled to PCI local bus 50 by ISA bridge 64. Coupled to ISA bus 62 is an input/output (I/O) controller 70, which controls communication between computer system 12 and attached peripheral devices such as a keyboard and mouse. In addition, I/O controller 70 supports external communication by computer system 12 via serial and parallel ports. A disk controller 72 is in communication with a disk drive 200. Of course, it should be appreciated that the system 12 may be built with different chip sets and a different bus structure, as well as with any other suitable substitute components, while providing comparable or analogous functions to those discussed above.

As further shown schematically in FIG. 1, system 12 may be encased in a system chassis and cover (jointly indicated at 152/154), the composition and functioning of which will be better understood from further discussion herebelow.

Figure 2:
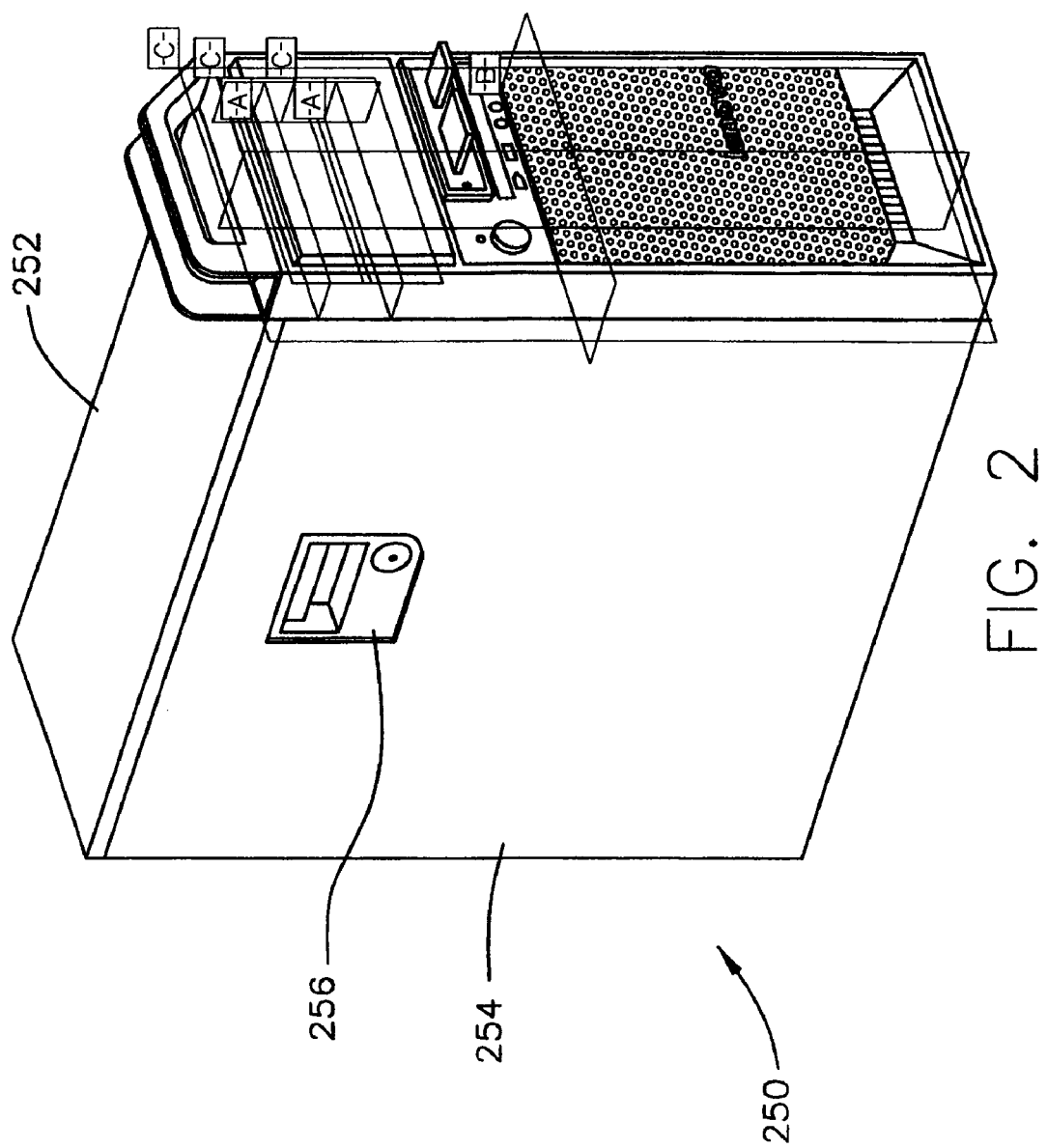
FIG. 2 provides a perspective front elevational view of a desktop.

FIG. 2 provides a perspective front elevational view of a desktop 250 in accordance with a presently preferred embodiment of the present invention. As shown, a cover 254, which more or less extends over a single planar surface of desktop 250, is integrated with a body or chassis 252. As is known, the cover 254 may be hingedly engaged with chassis 252 in such a way that it can pivot with respect to chassis 252; however, the hinged connection may be of a detachable variety whereby translational movement of the cover 254 with respect to the chassis 252 would disengage the former from the latter. Such hinged connections are well-known to those of ordinary skill in the computer arts and will not be further detailed herein.

Further shown in FIG. 2 is a latch mechanism 256 which, in accordance with a preferred embodiment of the present invention, facilitates removal of the cover 254 from chassis 252. This will be described in greater detail herebelow.

Figure 3:
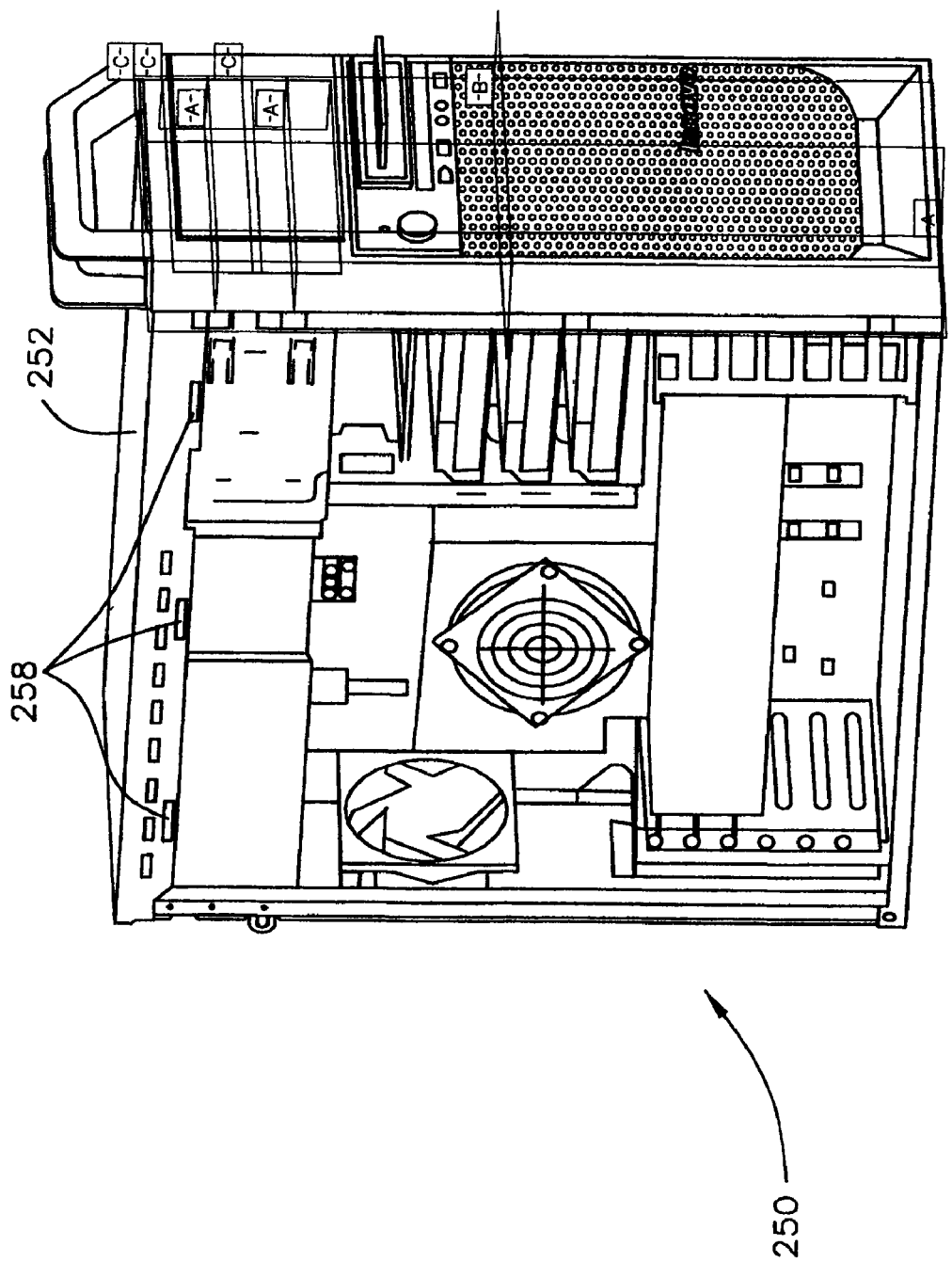
FIG. 3 depicts the desktop of FIG. 2 with a cover removed.

FIG. 3 depicts desktop 250 of FIG. 2 with the cover (254) removed. As shown, chassis 252 may be provided with slots 258 configured to receive hooks or detents of a lock bar (to be described further herebelow).

Figure 4:
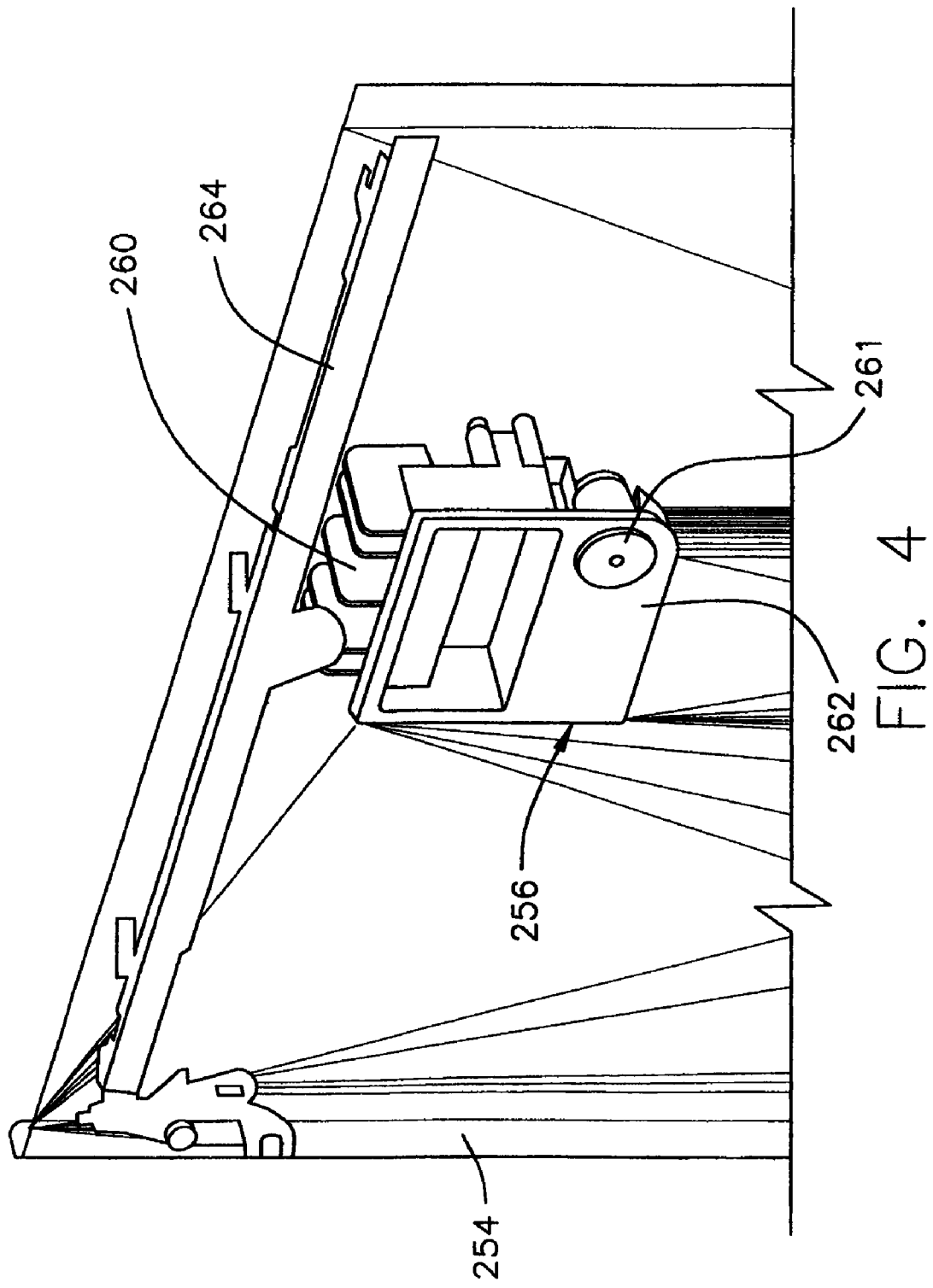
FIG. 4 depicts a cover from desktop of FIG. 2, with lock mechanism parts.

FIG. 4 depicts cover 254 semi-transparently (for the purposes of clearer illustration) along with other components. As shown, latch mechanism 256 as a whole may preferably be recessed with respect to the outer surface of cover 254. Preferably, a decorative handle portion 262 will be stationary with respective to cover 254 and will essentially serve as a mounting support for a release handle 260 (which alternatively may be termed a "handle", "release latch" or a "latch"). Handle 260 is preferably mounted to displace vertically (with respect to the drawing) in a manner to displace a lock bar 264, via an interaction of cam surfaces to be better understood herebelow. Also shown in FIG. 4 is a key lock 261 that is recessed in decorative handle portion 262. This may preferably be a standard, rotatable key lock; conventionally, such key locks have been employed to selectively decouple a cover from a chassis. However, as will be appreciated further below, key lock 261 preferably assumes here an expanded function.

Figure 5:
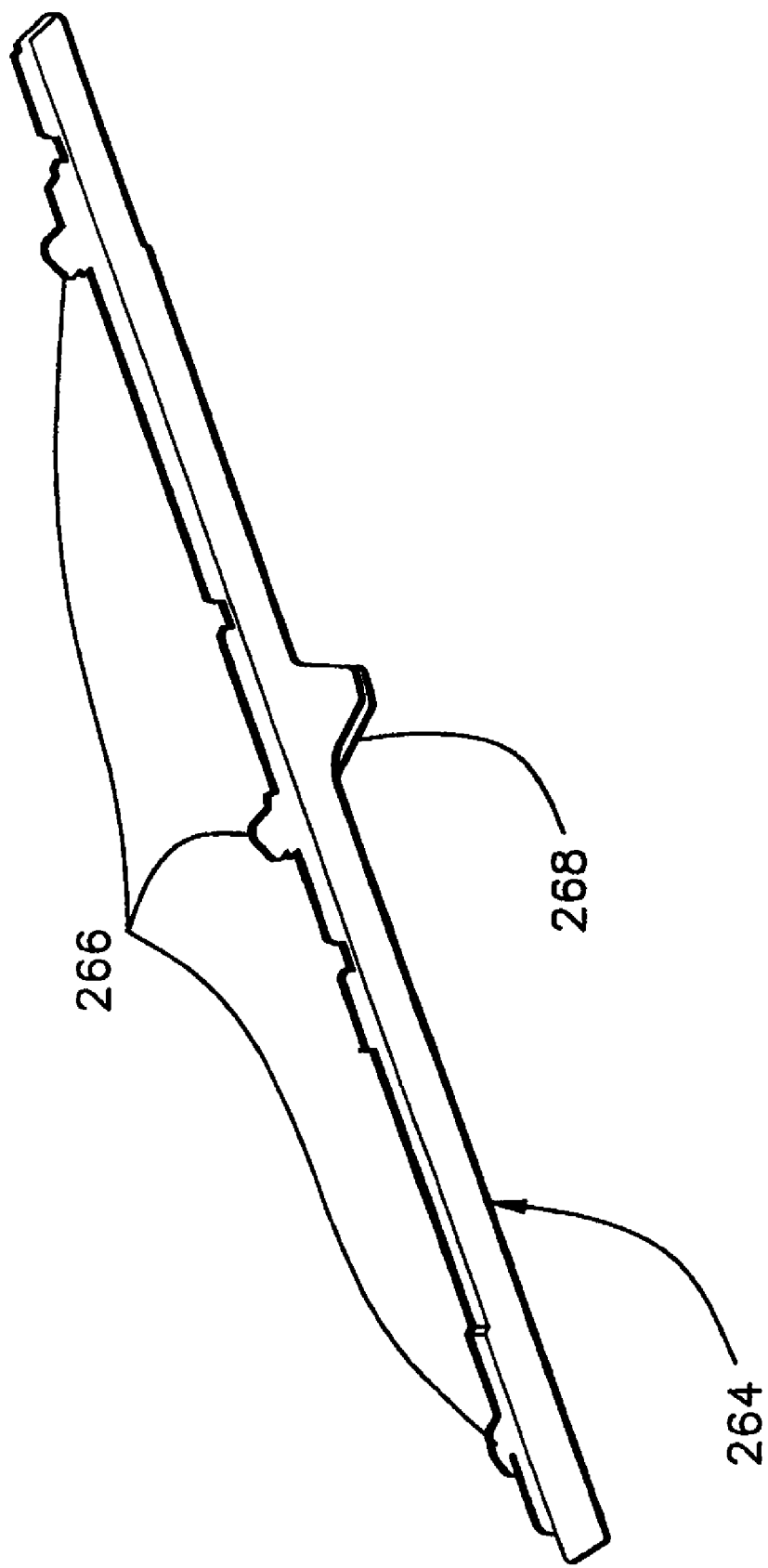
FIG. 5 illustrates, in perspective view, a lock bar.

Lock bar 264, for its part, is shown in isolation in FIG. 5. As shown, lock bar 264 preferably includes hooks or detents 266 that engage with slots 258 of the chassis 252 (see FIG. 3). Also shown in FIG. 5 is a cam surface 268 which enables the lock bar 264 to be displaced translationally, in a direction parallel to its longitudinal (i.e., longest) dimension.

Figure 6:
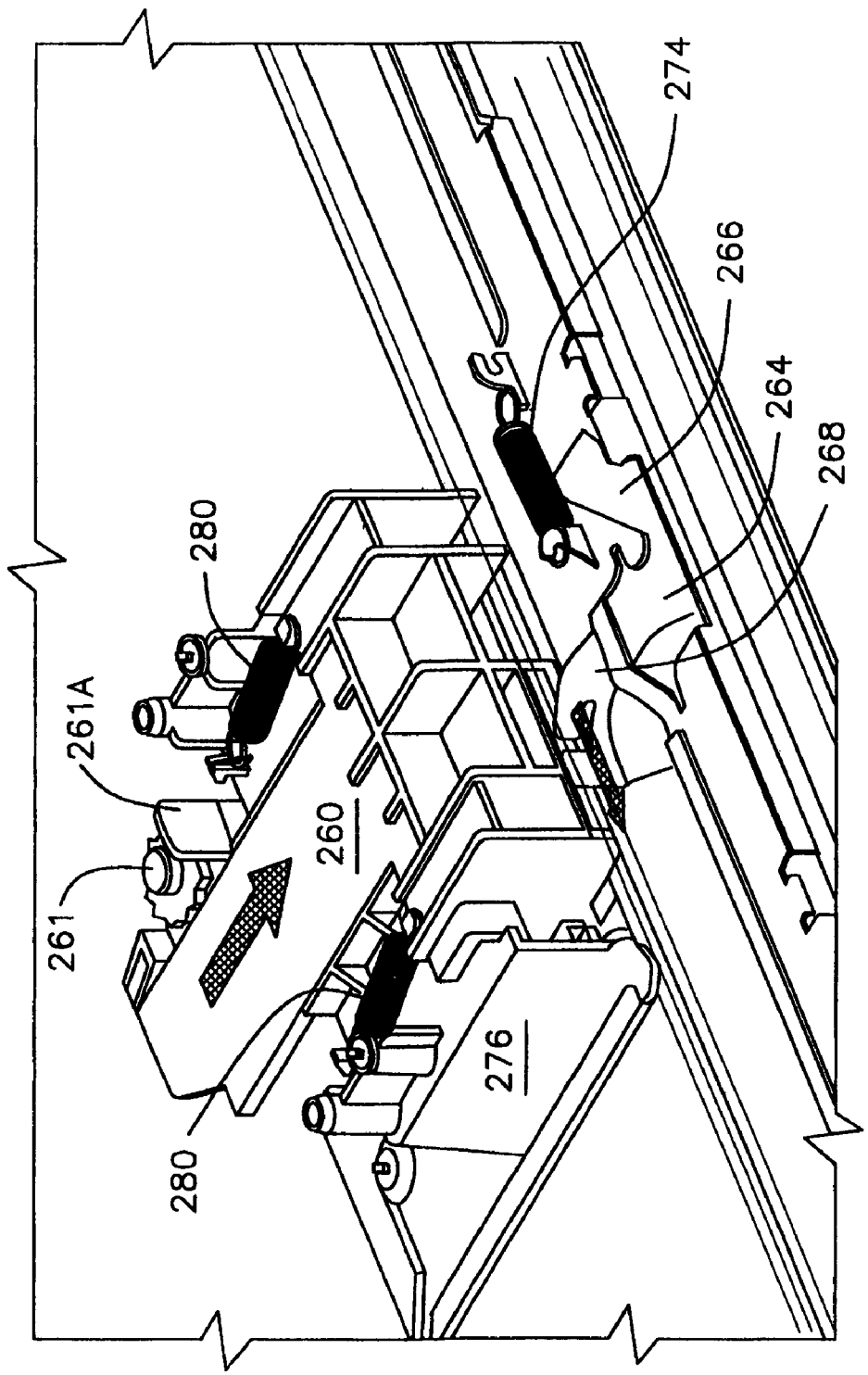
FIGS. 6 and 7 provide a perspective view of a latch mechanism and lock bar.
Figure 7:
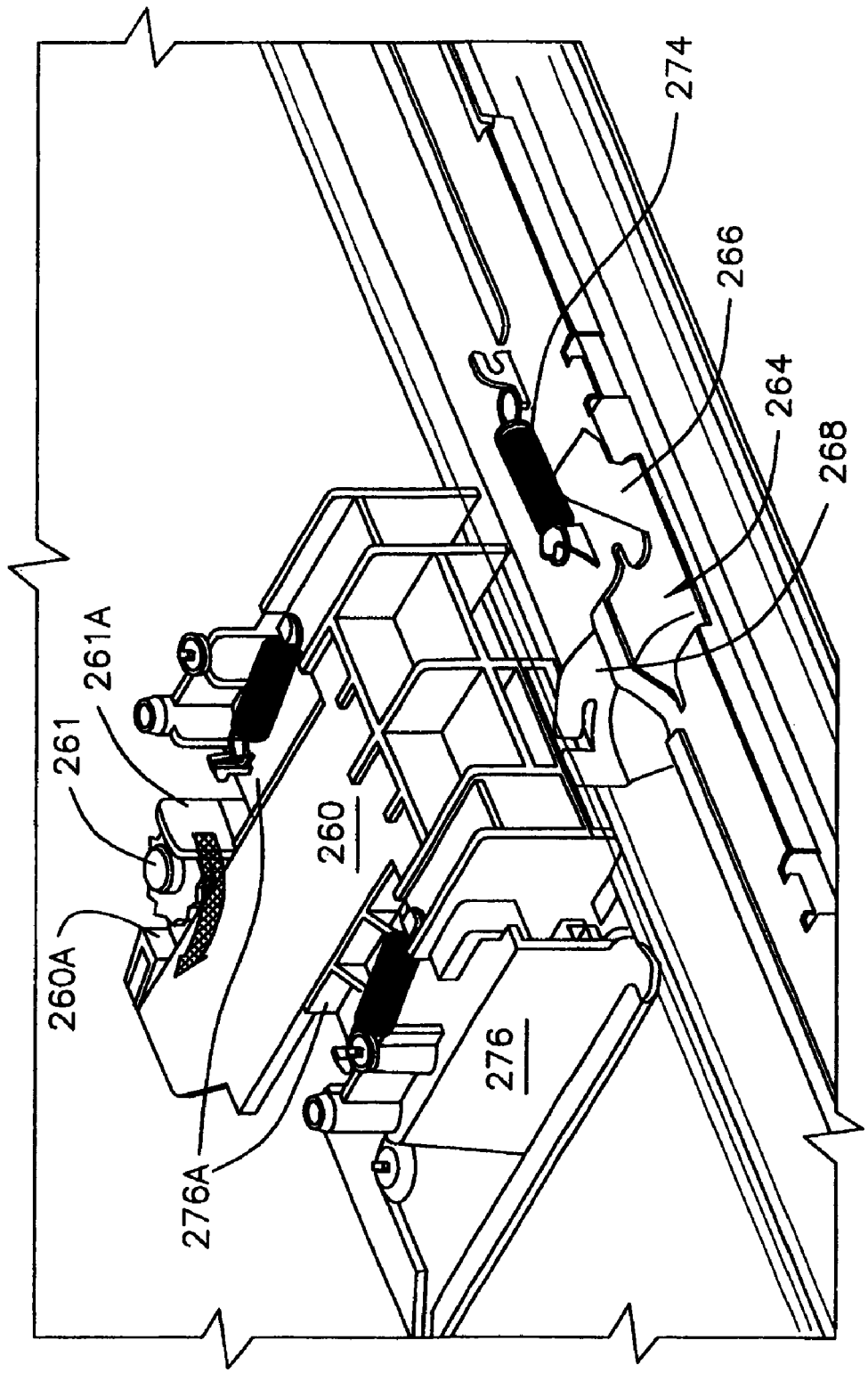

FIGS. 6 and 7 provide a perspective view of latch mechanism components and lock bar 264; both drawings will now be referenced jointly. As shown, latch or handle 260 is slidably mounted in a mounting plate 276 that essentially constitutes the rearward side of the decorative handle 262 (see FIG. 4). Mounting plate 276 preferably includes flanges and ribs configured for guiding the sliding movement of latch 260; two such ribs are indicated at 276a, and these immediately and snugly flank a central portion of latch 260. Preferably, latch 260 includes a cam surface (not shown here) configured for contacting and interacting with cam surface 268 of lock bar 264 as latch 260 is displaced towards lock bar 264. More particularly, as latch 260 is displaced in the direction of the arrow pointing downward and to the right in FIG. 6, the aforementioned interaction of cam surfaces will ensure that lock bar 264 is displaced towards the left in FIG. 6 (as indicated by a second arrow). Accordingly, this will release hooks/detents 266 from chassis slots (e.g., slots 258 shown in FIG. 3) such that the cover will now be able to be removed from the chassis.

It will be appreciated that this is accomplished by way of a quick and easy physical manipulation on the part of the user, whereby the user need only pull on the release latch 260 and then, essentially employing the same gripping action, remove the cover away from the chassis. This is in stark contrast to conventional arrangements where, e.g., once a cover is unlocked from a chassis via a key lock, a more cumbersome and inconvenient physical manipulation needs to be undertaken to separate the cover from the chassis; here, by virtue of the release latch 260 which can be pulled by a user's fingers while they are inserted into a recess in the cover (see especially the decorative handle 262 in FIG. 4, which includes a large recessed portion with respect to cover 254), it becomes much easier to physically support the cover with one's fingers or hand, and removing the cover from the chassis can even be accomplished solely with one hand.

As further shown, key lock 261 may preferably be provided with an extension 261a that is fixed with respect to a remainder of key lock 261. To lock the cover with respect to the chassis, as shown in FIG. 7, if a key is inserted in key lock 261 to then rotate key lock 261, e.g., about 90 degrees (here, in a clockwise direction as shown by the arrow), extension 261a will preferably travel with it. Latch 260, for its part, will preferably be provided with its own extension 260a that presents a surface which, when latch 260 is displaced towards lock bar 264, will come into contact with extension 261a of key lock 261, thereby preventing further displacement of latch 260 towards lock bar 264. Thus, inasmuch as FIGS. 6 and 7 depict an "unlocked" configuration, where latch 260 is free to slidingly displace to move lock bar 264, the aforementioned action of turning key lock 261, e.g., 90 degrees will have the effect of preventing interaction of latch 260 with lock bar 264, thus keeping the cover "locked" with respect to the chassis.

FIG. 7 also shows the aforementioned ribs 276a; it should be appreciated that these will preferably ensure that as key lock 261 and extension 261a undergo rotational displacement, latch 260 itself will not be displaced out of parallel to its usual direction of travel.

As also shown, a pair of springs 280 preferably are connected between latch 260 and mounting bracket 276 such that latch 260 will be biased back towards a rest position once it has been displaced towards lock bar 264. Further, a return spring 274 is preferably connected between lock bar 264 and a portion of the cover such that, after lock bar 264 has been translated to decouple hooks/detents 266 from chassis slots, the lock bar will be urged back towards a rest position of its own.

Figure 8:
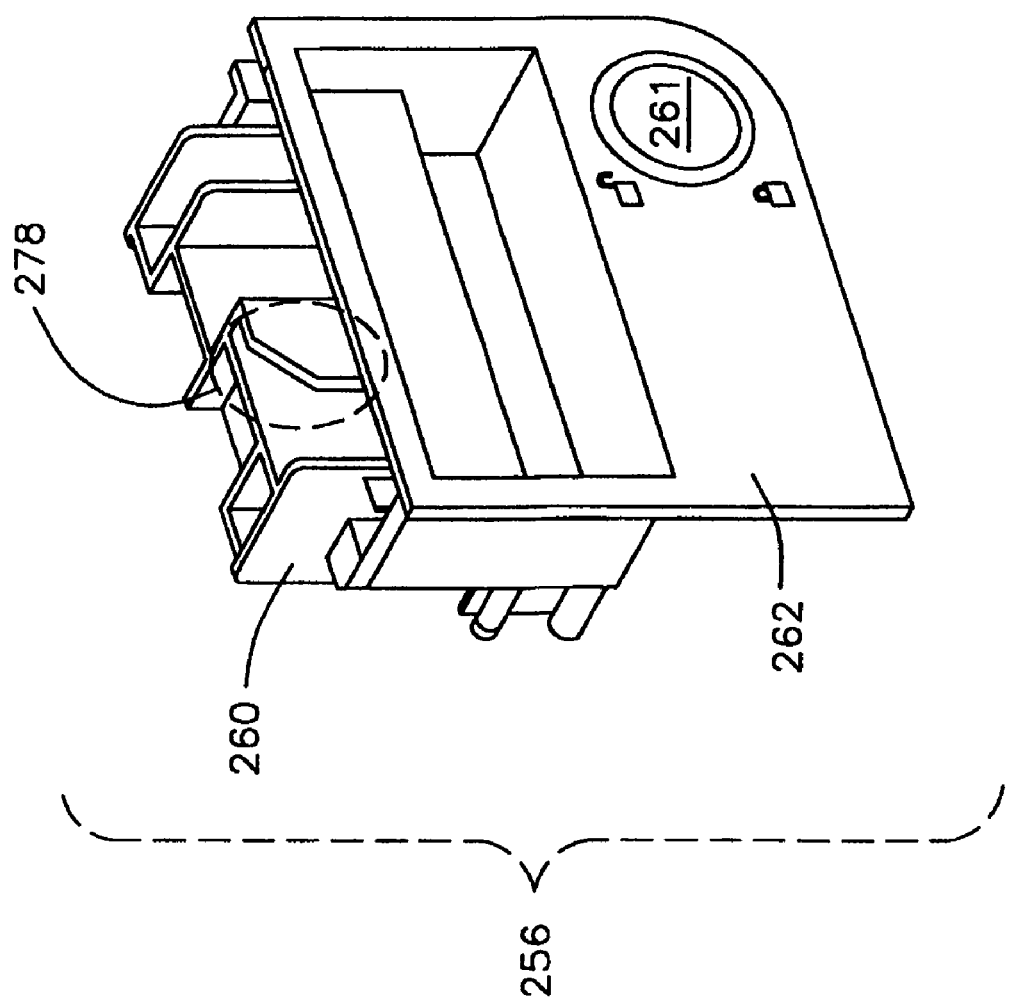
FIG. 8 provides a perspective view of a latch mechanism in isolation.

FIG. 8 provides a perspective view of a latch mechanism 256 in isolation. In addition to showing the key lock 261 as well as the latch 260 slidingly mounted with respect to decorative handle 262 (and, by extension, the mounting bracket 276 as depicted in FIGS. 6 and 7), FIG. 8 also shows a cam surface 178 which is configured to interact with the cam surface 268 of lock bar 264 (see FIGS. 5, 6 and 7). Preferably, cam surfaces 268 and 278 may be configured in any suitable manner to ensure that sliding displacement of latch 260 easily converts to a translational motion of lock bar 264 sufficient for decoupling detents/hooks 266 from chassis slots 258 (see FIG. 3).

Figure 9:
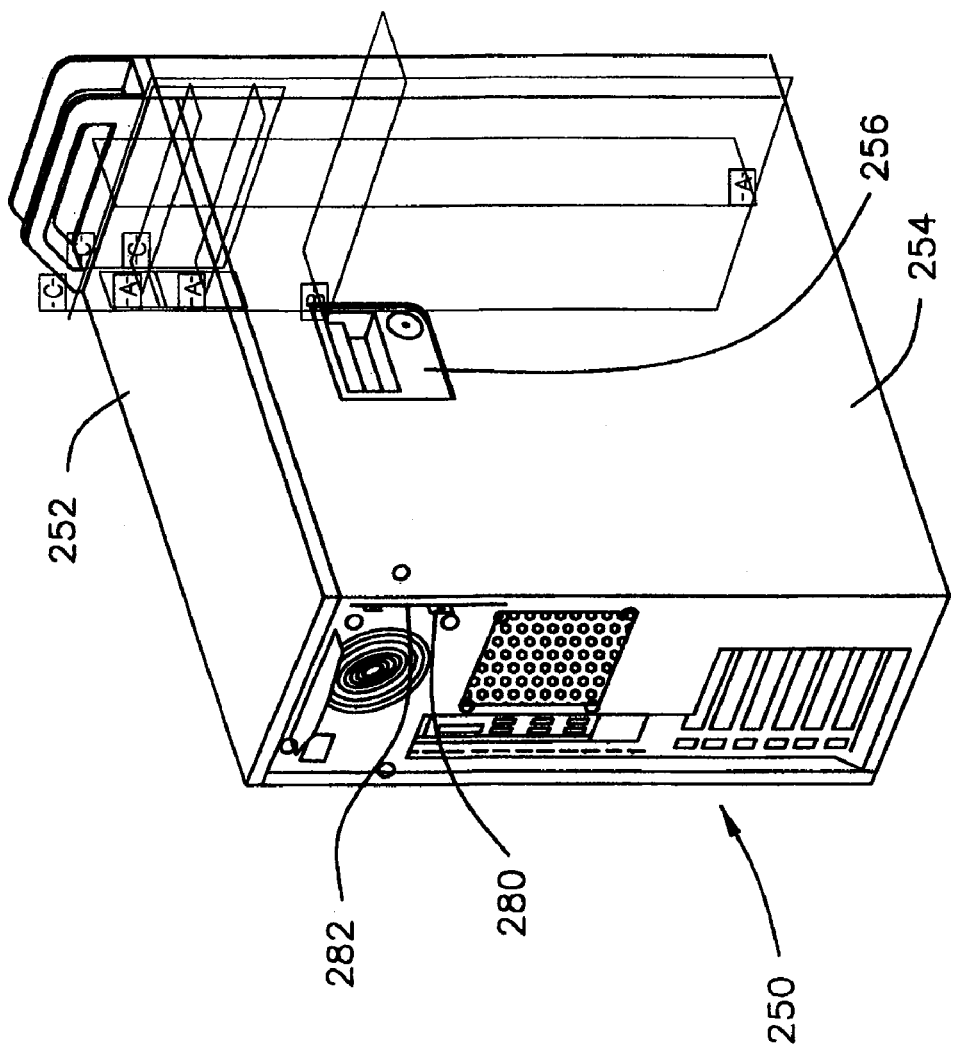
FIG. 9 provides a perspective rear elevational view of a desktop.

FIG. 9 provides a perspective rear elevational view of desktop 250. Cover 254, chassis 252 and latch mechanism 256 are once again depicted; however, also shown is a padlock hasp 280 and laptop lock slot 282 whose makeup and functioning will be discussed in more detail herebelow. Generally, as well known, a padlock hasp serves to secure a cover to a chassis at best superficially, in that a padlock inserted through the hasp does not necessarily prevent an unauthorized individual from prying or peeling a cover away from a chassis (absent other locking or securing arrangements). Accordingly, it is known to accompany a padlock hasp locking arrangement with a key locking arrangement. However, these two separate systems can be cumbersome to handle in conventional settings.

On the other hand, a laptop lock or Kensington lock acts in such a way that a locking cylinder that is integral with a cable (neither of which are shown here) has an extension for insertion into a slot such as that indicated at 282. This extension, as well known, then can serve to secure the cover to the chassis; further, the cable can be looped around a stationary object to ensure that the desktop as a whole cannot easily be removed. But, as with conventional padlock arrangements (as just discussed), the mere provision of a laptop/Kensington lock does not on its own preclude an unauthorized individual for prying a portion of a cover away from a chassis.

Figure 10:
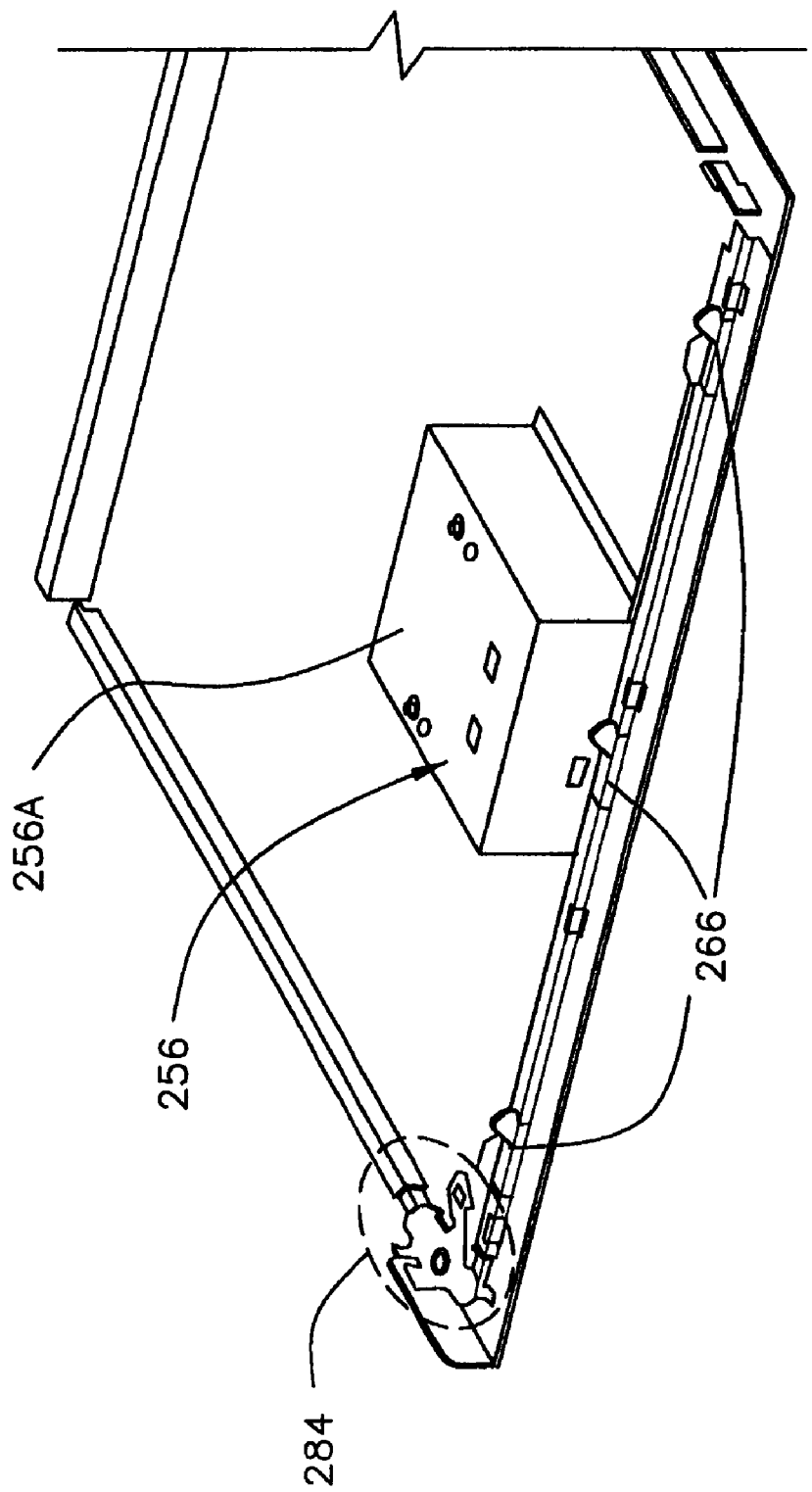
FIG. 10 provides a perspective view of a cover with a lock bar and rotating linkage.

FIG. 10 provides a perspective view of a cover with a lock bar and rotating linkage, in accordance with a preferred embodiment of the present invention. As shown a latch mechanism may be covered with its own cover 256a and may interact with a lock bar in a similar manner as discussed hereabove, or may interact with it in another way. Indicated at 284 is a rotating linkage disposed adjacent the slot 282 and is preferably integral with a padlock hasp 280 (see FIG. 9).

Figure 11:
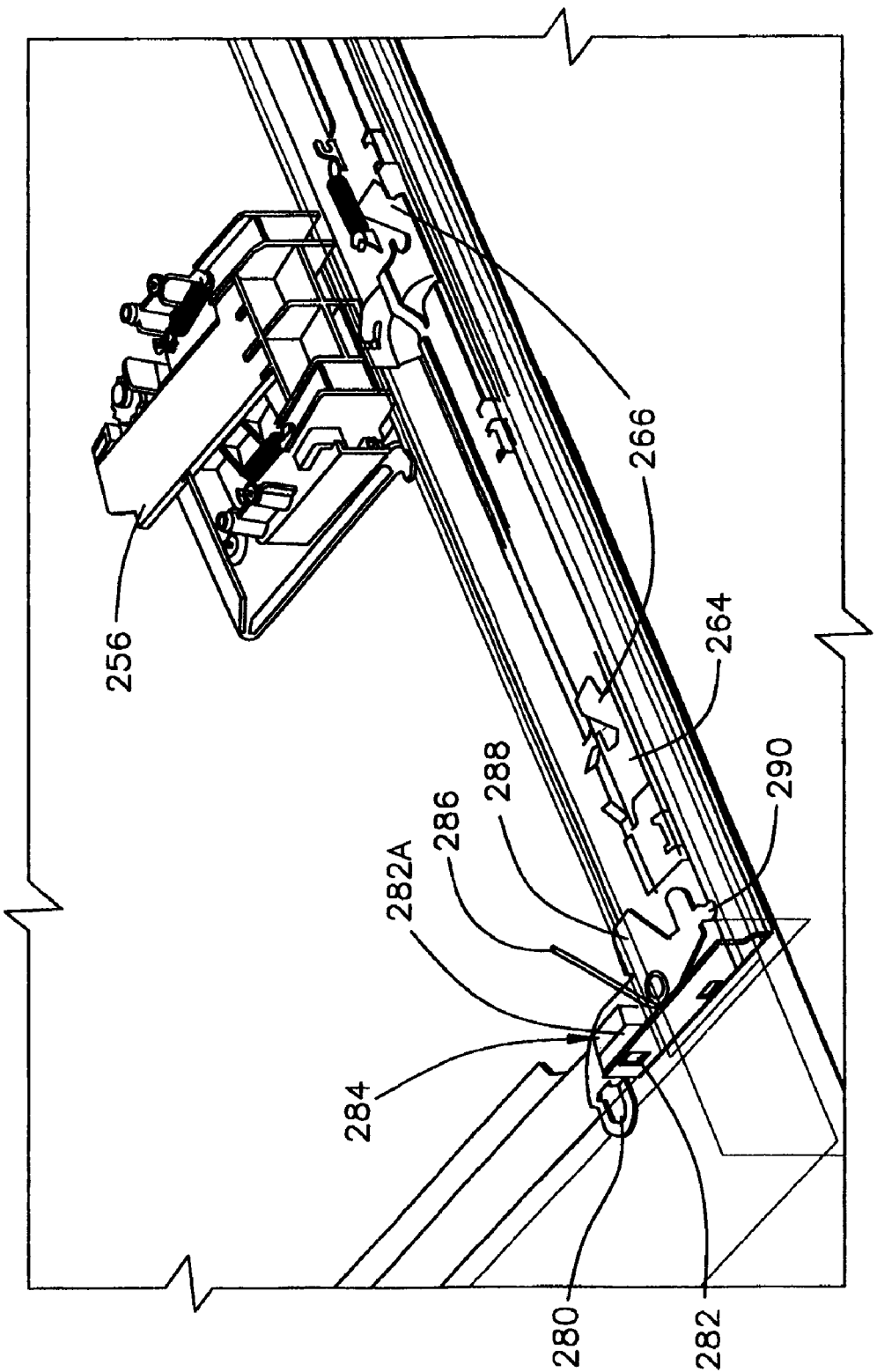
FIG. 11 provides another perspective view of the cover of FIG. 10 (but with a latch mechanism cover removed).
Figure 12:
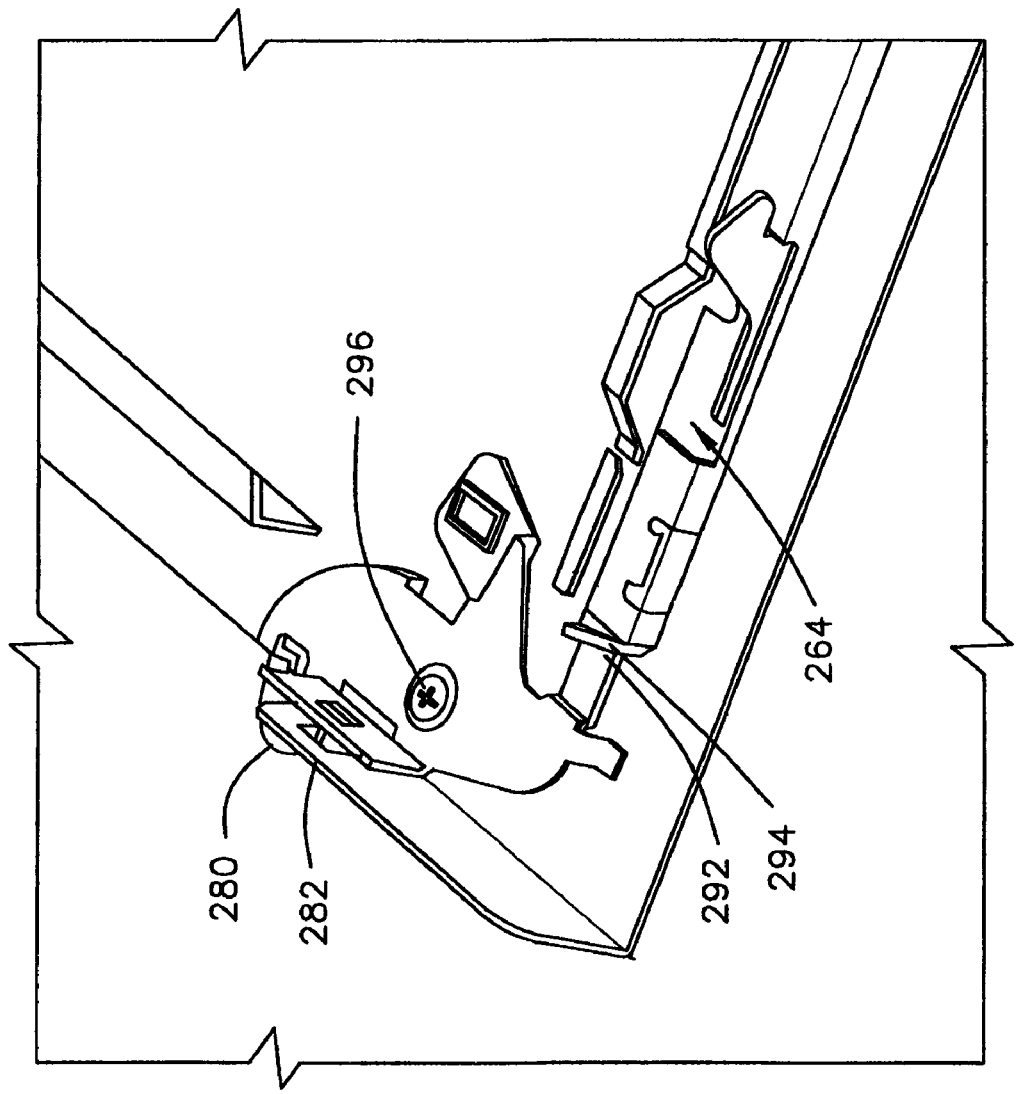
FIG. 12 provides a close-up perspective view of the rotating linkage from FIGS. 10 and 11.

FIG. 11 provides another perspective view of the cover of FIG. 10, but with the latch mechanism cover 256a removed, while FIG. 12 provides a close-up perspective view of the rotating linkage from FIGS. 10 and 11. Again, it should be understood that latch mechanism 256 could have similar components as discussed heretofore with regard to FIGS. 2-8, or potentially could include other components. FIGS. 10-12 will now be referred to jointly.

Preferably, rotating linkage 284 is a separate component from lock bar 264. Linkage 284, as shown, preferably includes a padlock hasp 280 directly integrated therewith, and also preferably includes a flange 282a that presents an aperture that aligns with slot 282. The linkage is preferably rotated about a pivot point (such as a shoulder screw) 296 and, preferably, is biased via a torsion spring 286 towards a "rest" position as depicted in FIGS. 11 and 12.

Preferably, when linkage 284 is free to rotate (i.e., it is not held in the rest position via a padlock through hasp 280 and/or via a laptop/Kensington lock as inserted through slot 282 and flange 282a), a translational movement of lock bar 264, in a direction generally towards the left of FIG. 11, will cause linkage 284 to rotate in a clockwise direction with respect to FIG. 11. Essentially, this freedom of rotational movement of linkage 284 will ensure that lock bar 264 can even translate to begin with.

As such, it should now be appreciated that if, indeed, a padlock is disposed through hasp 280 and/or if a laptop/Kensington lock is inserted in slot 282 and flange 282a, linkage 284 will be rotationally held in place and will prevent translational movement of lock bar 264. Accordingly, this functional cooperation of linkage 284 and lock bar 264 ensures that an engaged padlock or laptop/Kensington lock, by its own merit, will prevent an unauthorized user from even being able to pry away a cover from a chassis, as detents/hooks 266 of lock bar 264 will not be able to be disengaged from chassis slots.

Also shown in FIG. 11 are extensions 288 and 290 (provided here as illustrative and non-restrictive examples) which can help limit and/or guide the rotational displacement of linkage 284.

It should be appreciated that, with regard to the arrangements shown and described with respect to FIGS. 10-12, the makeup and functioning of latch mechanism 256 can be regarded as "generic", i.e., it need not necessarily be similar to the makeup and functioning of a latch mechanism as shown and described with respect to FIGS. 2-9. Accordingly, a primary focus of the arrangements shown and described with respect to FIGS. 10-12, i.e., essentially the manner via which a padlock and/or laptop/Kensington lock can serve to immobilize a lock bar such that, merely by virtue of the use of a padlock and/or laptop/Kensington lock, a much greater degree of physical securement of a cover with respect to a chassis takes place. By making these two locking/securing arrangements interdependent (i.e., an "external" system including a padlock and/or laptop/Kensington lock and an "internal" system involving a lock bar), cumbersome physical manipulations involving two separate and independent systems are fully obviated.

It should further be understood and appreciated that the padlock hasp 280 and laptop/Kensington lock slot 282 (and flange 282*a*) are shown here as being together merely for illustrative purposes. It is conceivable, of course, to provide solely a padlock arrangement for "external" locking, or solely a laptop/Kensington lock for the purpose; they need not necessarily be provided together.

By way of additional background to better understand the functioning of one or more of the embodiments of the present invention as broadly contemplated herein, a slot for use with a laptop lock or "Kensington lock" (which slot is often termed a "Kensington Security Slot" or a "K-Slot") is normally embodied by a small, metal-reinforced hole found on a very wide variety of small or portable computer and electronics equipment, such as laptops, computer monitors, desktop computers, gaming consoles, and video projectors. It is used for attaching a lock-and-cable apparatus such as those manufactured by Kensington Computer Products Group (Redwood Shores, Calif.), and as briefly discussed hereabove. The lock is generally secured in place with a key or other mechanical securing device, and is fixed with respect to (typically) rubberized metal cable that has a loop at its end for securement to a permanent object.

If not otherwise stated herein, it is to be assumed that all patents, patent applications, patent publications and other publications (including web-based publications) mentioned and cited herein are hereby fully incorporated by reference herein as if set forth in their entirety herein.

Although illustrative embodiments of the present invention have been described herein with reference to the accompanying drawings, it is to be understood that the invention is not limited to those precise embodiments, and that various other changes and modifications may be affected therein by one skilled in the art without departing from the scope or spirit of the invention.

What is claimed is:

1. An apparatus comprising:
a main memory;
a system processor;
a chassis;
a cover which is displaceable with respect to said chassis;
said chassis and cover combining to substantially encase said main memory and system processor;
a decoupling arrangement which selectively decouples said cover with respect to said chassis;
a latch mechanism mounted at said cover;
said latch mechanism comprising a latch which is displaceable with respect to said cover;
said latch and said decoupling arrangement being operatively connected such that:
in a first position of said latch, said decoupling arrangement couples said cover to said chassis; and
in a second position of said latch, said decoupling arrangement decouples said cover from said chassis;
said latch mechanism further comprising a locking arrangement which selectively locks and unlocks said latch, wherein:
in a first configuration of said locking arrangement, said latch is not free to displace from said first position to said second position; and
in a second configuration of said locking arrangement, said latch is free to displace from said first position to said second position;
wherein said latch mechanism comprises a mount which displaceably mounts said latch with respect to said cover;
said mount being recessed into said cover.

2. The apparatus according to claim 1, wherein said decoupling arrangement comprising a lock bar which is slidably displaceable with respect to said cover.

3. The apparatus according to claim 2, wherein said lock bar is slidable between a first setting, wherein said lock bar couples said cover to said chassis, and a second setting, wherein said lock bar decouples said cover from said chassis.

4. The apparatus according to claim 2, wherein said lock bar acts to couple said cover to said chassis at a plurality of coupling points between said cover and said chassis.

5. The apparatus according to claim 4, wherein:
said locking bar comprises detents; and
said chassis comprises slots for receiving said detents.

6. The apparatus according to claim 1, wherein said locking arrangement comprises a key lock.

7. The apparatus according to claim 1, wherein:
said locking arrangement comprises an first extension; and
said latch comprises a second extension;
said first extension inhibits movement of said second extension in said first configuration of said locking arrangement.

8. The apparatus according to claim 1, further comprising a biasing arrangement which biases said latch towards said first position.

9. The apparatus according to claim 1, wherein:
said latch comprises a first contact surface, for contacting said decoupling arrangement; and
said decoupling arrangement comprises a second contact surface for contacting said latch;
said second contact surface contacting said first contact surface to move said decoupling arrangement from said first setting to said second setting as said latch displaces from said first position to said second position.

10. The apparatus according to claim 1, further comprising a biasing arrangement for biasing said decoupling arrangement towards a position wherein said decoupling arrangement couples said cover to said chassis.

11. The apparatus according to claim 1, wherein said latch is slidably mounted with respect to said mount.

12. The apparatus according to claim 1, wherein said mount provides a clearance such that, when said latch is in said first position, said latch is adapted for being manually displaced from said first position towards said second position.

13. The apparatus according to claim 12, wherein said latch retracts into said cover as said latch displaces from said first position towards said second position.

14. The apparatus according to claim 13, wherein said first and second contact surfaces comprise cam surfaces.

15. The apparatus according to claim 1, wherein said latch is slidably mounted with respect to said cover.

16. A method of removing a computer cover, said method comprising:
  providing a chassis having therein a main memory and a system processor;
  providing a cover which is displaceable with respect to the chassis;
  said chassis and cover combining to substantially encase said main memory and said system processor;
  providing a decoupling arrangement which selectively decouples the cover with respect to the chassis;
  providing a latch displaceably mounted with respect to the cover;
  operatively connecting the latch and the decoupling arrangement such that:
    in a first position of the latch, the decoupling arrangement couples the cover to the chassis; and
    in a second position of the latch, the decoupling arrangement decouples the cover from the chassis;
  coupling the cover with respect to the chassis;
  locking the latch into the first position;
  unlocking the latch to permit the latch to displace from the first position to the second position; and
  thereafter displacing the latch from the first position to the second position to thereby cause the decoupling arrangement to decouple the cover with respect to the chassis;
  wherein said latch comprises a mount which displaceably mounts said latch with respect to said cover;
  said mount being recessed into said cover.

17. The method according to claim 16, wherein said coupling comprises coupling the cover to the chassis at a plurality of coupling points between the cover and the chassis.

18. The method according to claim 16, further comprising biasing the latch towards the first position.

19. The method according to claim 16, further comprising biasing the decoupling arrangement towards coupling the cover to the chassis.

20. The method according to claim 16, wherein:
  said providing of the latch comprises providing a cam surface on the latch;
  said providing of the decoupling arrangement comprises providing a cam surface on the decoupling arrangement;
  the cam surface of the latch and the cam surface of the decoupling arrangement being cooperable with one another such that, as the latch moves from the first position to the second position, the decoupling arrangement moves to decouple the cover from the chassis.

* * * * *